United States Patent
Murru et al.

[11] Patent Number: 5,922,862
[45] Date of Patent: Jul. 13, 1999

[54] PROCESS FOR THE PREPARATION OF TETRAAZAMACROCYCLES

[75] Inventors: Marcella Murru; Emanuela Panetta; Fulvio Uberti; Andrea Beltrami; Giorgio Ripa, all of Milan, Italy

[73] Assignee: Dibra S.p.A., Milan, Italy

[21] Appl. No.: 09/121,674

[22] Filed: Jul. 23, 1998

[30] Foreign Application Priority Data

Jul. 21, 1997 [IT] Italy .................. MI97A1765

[51] Int. Cl.$^6$ ............................... C07D 257/02
[52] U.S. Cl. ........................... 540/474; 540/460
[58] Field of Search ............................ 540/474

[56] References Cited

U.S. PATENT DOCUMENTS

| | | | |
|---|---|---|---|
| 5,589,595 | 12/1996 | Sandnes et al. | 540/474 |
| 5,747,000 | 5/1998 | Platzek et al. | 424/9.363 |
| 5,756,065 | 5/1998 | Wilson et al. | 424/1.53 |

*Primary Examiner*—Mukund J. Shah
*Assistant Examiner*—Pavanaram K. Sripada
*Attorney, Agent, or Firm*—Nixon & Vanderhye P.C.

[57] ABSTRACT

A process for the preparation of the compounds of formula (I), and (II) comprising the steps represented in the following Scheme, in which the substituents are as defined in the specification.

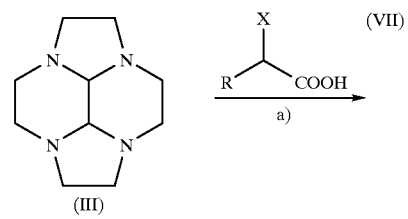

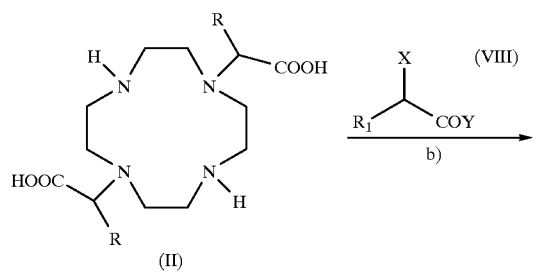

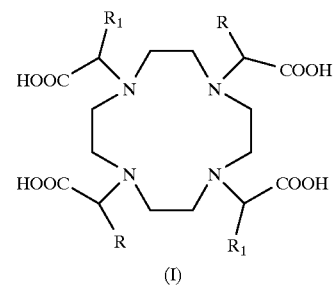

25 Claims, No Drawings

PROCESS FOR THE PREPARATION OF TETRAAZAMACROCYCLES

The present invention relates to a novel process for the preparation of 1,4,7,10-tetraazacyclododecane-1,4,7,10-tetraacetic acid derivatives of general formula (I) and of 1,4,7,10-tetraazacyclododecane-1,7-diacetic acid derivatives of general formula (II), starting from 2a,4a,6a,8a-decahydrotetraazacyclopent[fg]acenaphthylene of formula (III):

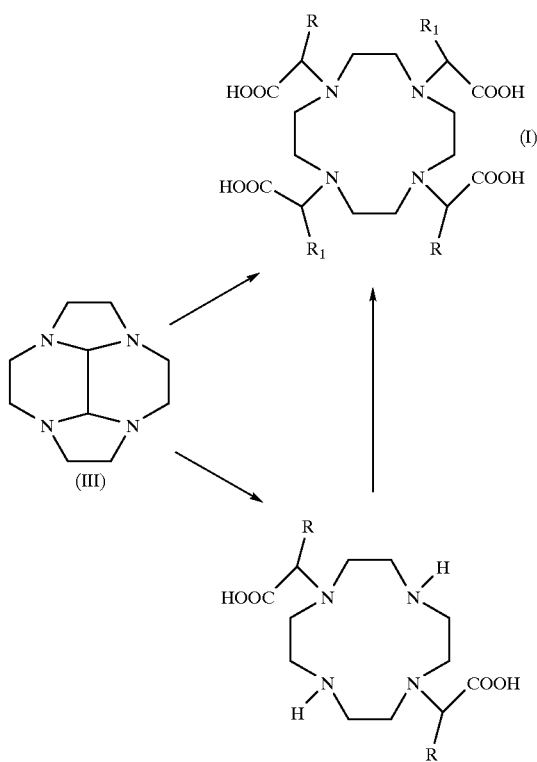

in which

R is a hydrogen atom, a straight, branched or cyclic $C_1$–$C_6$ alkyl group, unsubstituted or substituted with 1 to 10 oxygen atoms, $R_1$ independently of R, has the same meanings as R, or is a group $R_2$, in which $R_2$ is a $C_1$–$C_{20}$ alkyl group, optionally interrupted by a phenylene, a phenyloxy or phenylenedioxy, in its turn substituted with a straight or branched $C_1$–$C_6$ alkyl group, unsubstituted or substituted with 1 to 7 hydroxy groups or 1 to 3 $C_1$–$C_7$ groups; the aromatic group can be unsubstituted or substituted with alkoxy groups or halogens, carboxy, carbamoyl, alkoxycarbonyl, sulfamoyl, hydroxyalkyl, amino, acylamino, acyl, hydroxyacyl groups;

which compounds are useful as chelating agents of paramagnetic metal ions for the preparation of macrocyclic complexes, which are used in the medical diagnostic field as contrast agents for magnetic resonance tomography.

Particularly preferred is the process of the present invention for the preparation of 1,4,7,10-tetraazacyclododecane-1,4,7,10-tetraacetic acid of formula (IV) and of 1,4,7,10-tetraazacyclododecane-1,7-diacetic acid of formula (V) (also named DO2A), according to the following scheme:

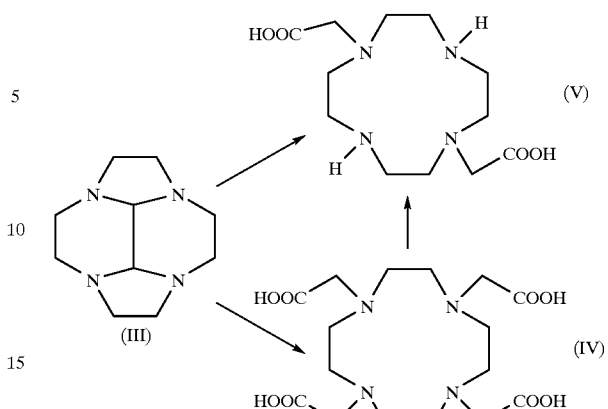

1,4,7,10-Tetraazacyclododecane-1,4,7,10-tetraacetic acid of formula (IV) includes, among its various synthetic applications, the use thereof for the preparation of Dotarem® (gadolinium complex of 1,4,7,10-tetraazacyclododecane-1,4,7,10-tetraacetic acid meglumine salt), a commercially available contrast agent for magnetic resonance tomography, and it can be prepared starting from 1,4,7,10-tetraazacyclododecane of formula (VI) by reaction with a haloacetic acid.

This synthesis, although not particularly complex, makes use, however, of compound (VI) as starting material, which is not easy to prepare. For example, 1,4,7,10-tetraazacyclododecane can be synthesized conventionally, according to the procedure by Richman-Atkins (see for example U.S. Pat. No. 4,085,106), which is based on the use of tosyl derivatives. This synthesis is poorly attractive for industrial processes, mainly for economic and environmental reasons, due to the type of wastes to be disposed, which contain large amounts of p-toluenesulfonic acid and of inorganic salts.

Possible alternatives to Richman-Atkins's synthesis are synthetic approaches starting from triethylenetetraamine, such as the process described in WO 95/14726, or that according to WO 96/28432 as well as those described in Italian Patent application MI 96A 001257.

These synthesis do not make use of polyamines tosyl derivatives, and they are based on the preparation of polycyclic intermediates which can be converted to the desired macrocycle in hydrolytic (WO 95/14726; WO 96/28432) or oxidizing (MI 96A 001257) conditions, as summarized in the following:

WO 95/14726

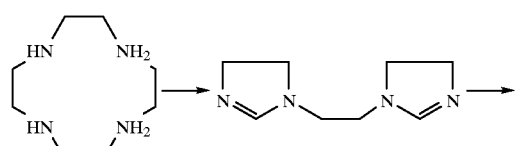

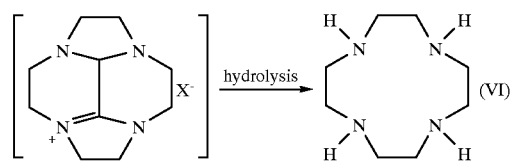

WO 96/28432

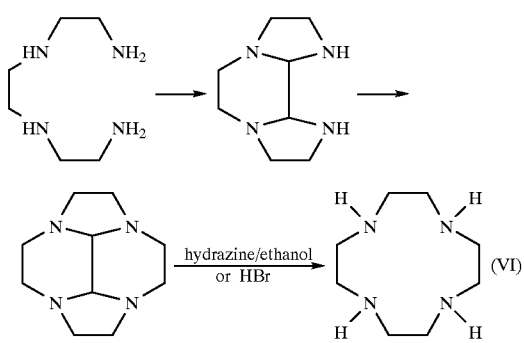

MI 96A 001257

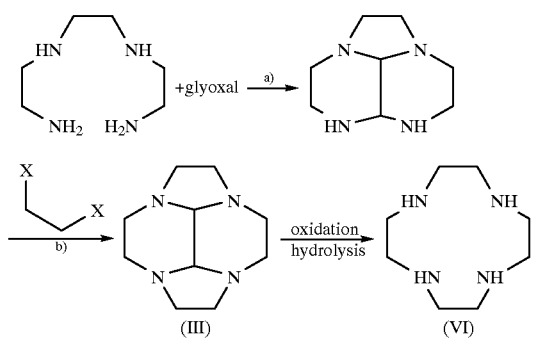

When 1,4,7,10-tetraazacyclododecane disubstituted derivatives, such as the acid of formula (V), are desired, the synthetic route starting from macrocycle (VI) is extremely complex, as it is described, for example, in WO 93/12097, and is based on a series of selective protections, which use reactives poorly suitable for any industrial applications, above all due to economic and environmental reasons.

WO 93/12097

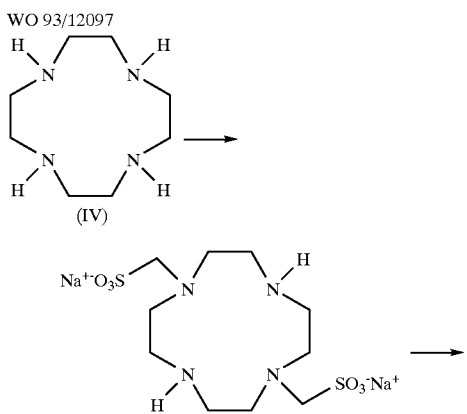

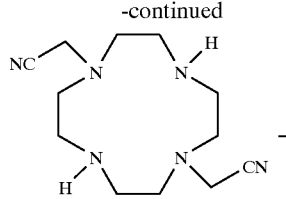

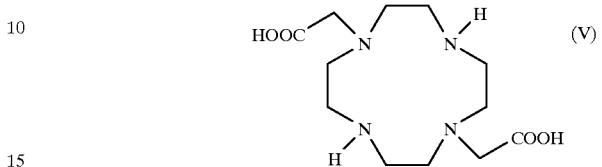

(V)

What stated above clearly shows that synthetic routes to compound (IV) or to compound (V), which do not require the use of 1,4,7,10-tetraazacyclododecane (VI), would, on one hand, be a remarkable improvement in the processes for the synthesis of Dotarem®, and, on the other hand, open a way to the preparation of novel contrast agents for magnetic resonance tomography, which are, at present, available with difficulty due to the above cited selectivity problems characterising the conversion of (VI) to (V).

It has now surprisingly been found, and this is the object of the present invention, a process for the preparation of the compounds of general formula (I), comprising the steps represented in Scheme 1:

Scheme 1

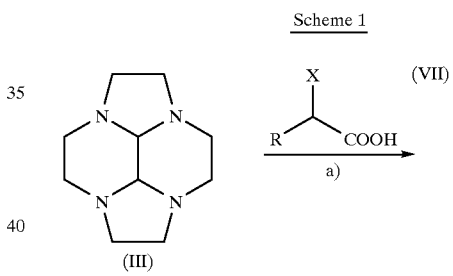

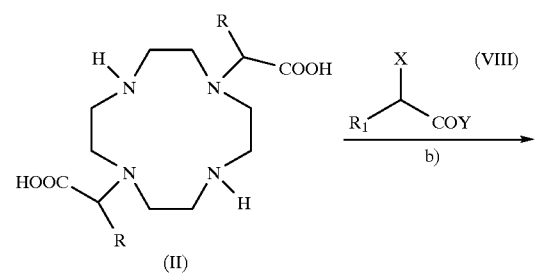

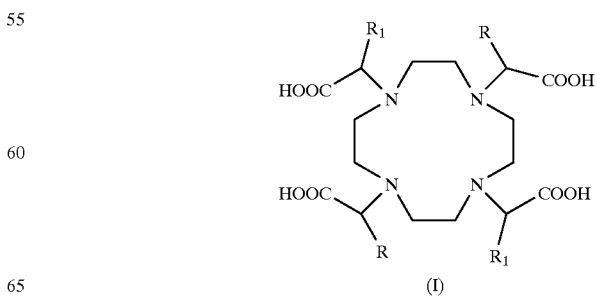

R is a hydrogen atom, a straight, branched or cyclic $C_1$–$C_6$ alkyl group, unsubstituted or substituted with 1 to 10 oxygen atoms, $R_1$ independently of R, has the same meanings as R, or is a group $R_2$, in which $R_2$ is a $C_1$–$C_{20}$ alkyl group, optionally interrupted by a phenylene, phenyloxy or phenylenedioxy, in its turn substituted with a straight or branched $C_1$–$C_6$ alkyl group, unsubstituted or substituted with 1 to 7 hydroxy groups or 1 to 3 $C_1$–$C_7$ groups; the aromatic group can be unsubstituted or substituted with alkoxy groups or halogens, carboxy, carbamoyl, alkoxycarbonyl, sulfamoyl, hydroxyalkyl, amino, acylamino, acyl, hydroxyacyl groups;

X is a halogen or a sulfonic acid reactive residue, and

Y is a —OH, or —$OR_3$ group, wherein $R_3$ is a straight or branched, $C_1$–$C_4$ alkyl group, and in which:

step a) is the alkylation reaction of compound (III) with the acid of general formula (VII), in aqueous solution and at basic pH, to give the compounds of general formula (II), and step b) is the alkylation reaction of compounds formula (II), according to known methods, with an $R_1$—CH(X)—COY alkylating agent of general formula (VIII), followed by a hydrolysis reaction of any ester groups present, to give the compounds of general formula (I).

When Y is —$OR_3$, a hydrolysis step of the ester groups, according to known methods, is also included, so as to obtain the compounds of formula (I). In this case, it may be convenient to also transform the acid group present in compound (II) into the ester group —$OR_3$, to promote the alkylation reaction, depending on the reactivity of the alkylating agent itself.

The amount of alkylating agent of general formula (VII) or (VIII) used in step a) ranges from 2 to 2.3 mols of reagent per mol of substrate and, in step b), it ranges from 2 to 3 mols of reagent per mol of substrate.

The reaction temperature in step a) and in step b), when $R_1$ is the same as R, ranges from room temperature to 80° C., depending on the reactivity of the selected alkylating agent, in the conditions indicated.

The basic pH in step a) and in step b), in case the alkylating agent of formula (VIII) is an acid, is preferably obtained by addition of an alkali or alkaline-earth metal hydroxide to the aqueous solution of compounds (III) and (II).

Particularly preferred are sodium and potassium hydroxides.

On the other hand, when the alkylation reaction is carried out with an ester derivative of compound (VIII), the reaction solvent can be suitably selected from dipolar aprotic solvents, in particular dimethylformamide (DMF), dimethylacetamide (DMA), dimethylsulfoxide (DMSO), acetonitrile ($CH_3CN$) and N-methylpyrrolidone, and the reaction is carried out in the presence of an organic base, preferably an aliphatic tertiary amine selected from triethylamine (TEA), diisopropylethylamine and tributylamine.

The reaction temperature can range, in this case, from 0 to 80° C., depending in any cases on the reactivity of the selected alkylating agent.

In this case, the alkylation reaction will be followed by basic hydrolysis of the resulting diester, in conventional conditions, to obtain the desired compound of general formula (I).

The alkylating agents of general formula (VII) or (VIII) can be selected from the compounds which either are already commercially available or can be prepared as already described in literature (see for example WO 93/24469 or EP 325762), or, among those still to be synthesized, using for example known methods for the preparation of suitable precursors (e.g. for acid chlorides α-halogen derivatives see: Harpp et al., J. Org. Chem., 40, 3420, 1975), and subsequent transformation into the desired product.

Preferably, R can be selected from the group consisting of: H or a straight or branched alkyl group, such as a methyl, ethyl, propyl, isopropyl, butyl, isobutyl group, in its turn substituted with hydroxy groups or interrupted by oxygen atoms, as defined above.

$R_2$ can preferably be selected from the group consisting of: phenyl, benzyl, phenylmethoxymethyl.

$R_3$ can preferably be selected from the group consisting of: methyl, ethyl, isopropyl, butyl, tert-butyl.

The reactive group X can be selected, for example, from the group consisting of halogens (Cl, Br, I), or it is the mesylate group ($MeSO_2O^-$), the benzenesulfonyloxy group ($PhSO_2O^-$), the nitrobenzenesulfonyloxy group (p-$NO_2PhSO_2O^-$), the tosylate group ($TsO^-$), the triflate group ($CF_3SO_3^-$).

Particularly preferred are the compounds in which X is a halogen, more particularly a bromide.

Particularly preferred are the alkylating agents of formula (VII) or (VIII) corresponding to bromoacetic acid (commercially available product), 2-bromopropionic acid (commercially available product), 2-bromobutyric acid (commercially available product).

When $R_2$ is present in the alkylating agent of general formula (VIII), particularly preferred are 3-(phenylmethoxy)propanoic acid reactive derivatives, such as 2-bromo-3-(phenylmethoxy)propanoic acid, the preparation of which is described in Grossman et al., Chem. Ber., 91, 538, 1958, and 2-chloro-3-(phenylmethoxy)propanoic acid (CAS RN 124628-32-6), prepared analogously to the brominated derivative, or the corresponding esters thereof and the triflate derivatives thereof at the 2- position, most preferred being 2-bromo-3-(phenylmethoxy)propanoic acid or 2-trifluoromethanesulfonate-3-(phenylmethoxy) propanoic acid methyl ester.

Particularly preferred is the process, according to scheme 1, for the preparation of compounds (IX), 1,4,7,10-tetraazacyclododecane-1,7-diacetic acid derivatives, as represented in the following Scheme 2:

Scheme 2

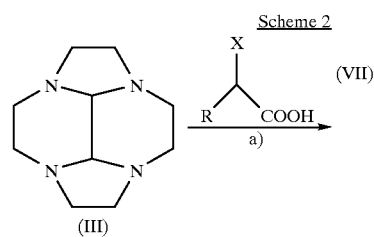

-continued

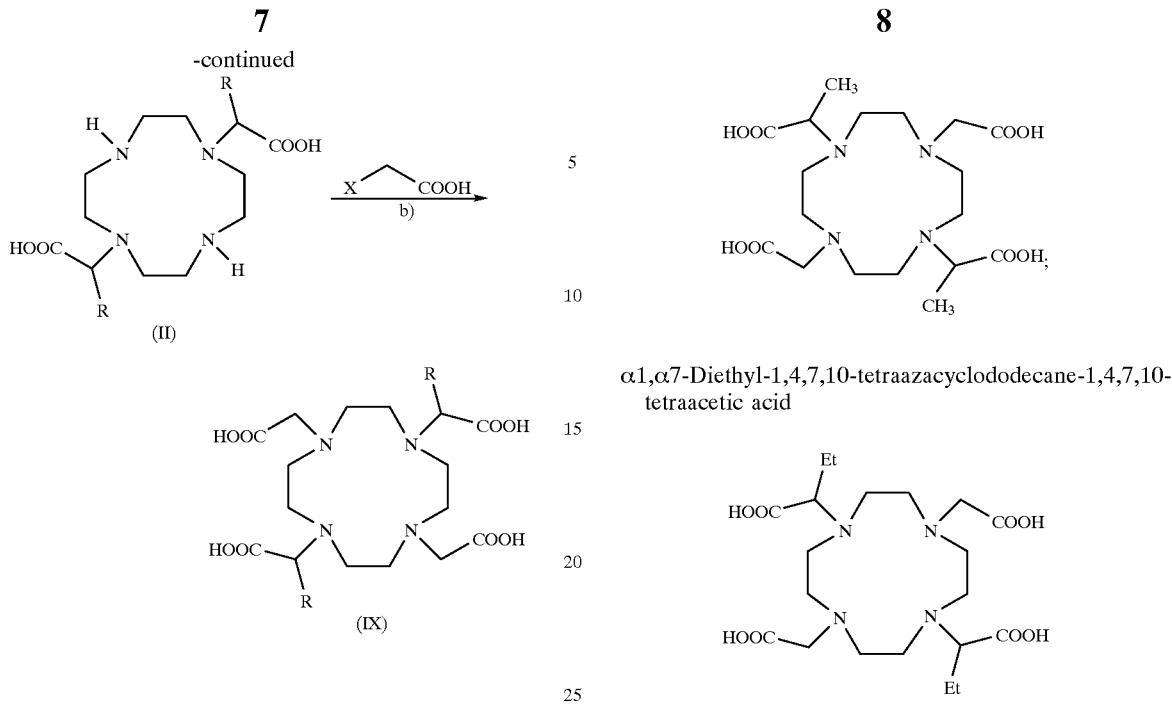

in which R and X have the meanings defined above, and step b) is the alkylation reaction of compounds (II), in aqueous solution at basic pH, with an excess of an alkylating agent X—CH$_2$COOH, to give compounds (IX).

Examples of compounds of general formula (II) and (IX), the preparation of which, according to scheme 2, is reported in the Experimental section, are the following:

α,α'-Dimethyl-1,4,7,10-tetraazacyclododecane-1,7-diacetic acid

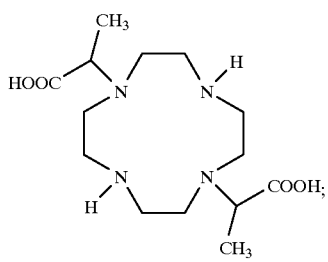

α,α'-Diethyl-1,4,7,10-tetraazacyclododecane-1,7-diacetic acid

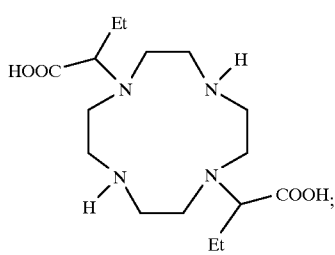

α1,α7-Dimethyl-1,4,7,10-tetraazacyclododecane-1,4,7,10-tetraacetic acid

α1,α7-Diethyl-1,4,7,10-tetraazacyclododecane-1,4,7,10-tetraacetic acid

Particularly preferred is the process, according to scheme 1, for the preparation of compound (V) by alkylation of compound (III), in which the alkylating agent of formula (VII) corresponds to an acetic acid derivative XCH$_2$COOH, as represented in Scheme 3.

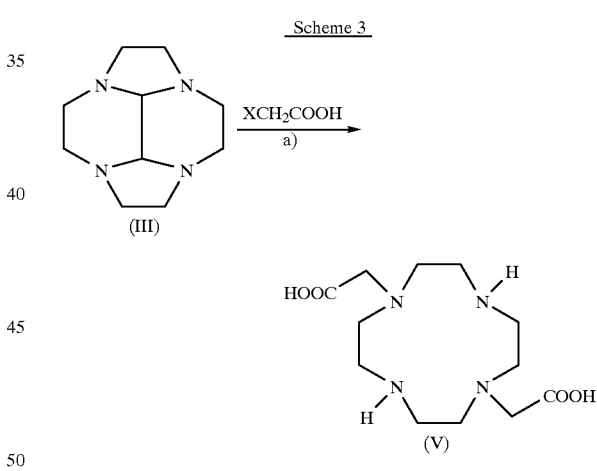

The conversion of compound (III) to compound (V) involves heating of (III) in aqueous solution at temperatures ranging from 25° C. to 50° C., at basic pH (preferably pH 10–11), in the presence of a haloacetic acid added in amounts of 2 mol/mol of compound (III). At the end of the reaction, the mixture is neutralized and concentrated to dryness.

The residue can be purified from inorganic anions by ion exchange. Eluates are suitably concentrated to dryness, to obtain a product at high quality (HPLC assay >97%), which can optionally be recrystallized from acetone-methanol, to obtain a purity higher than 99% (HPLC assay).

The resulting compound of formula (V) can then be preferably alkylated with compound (VIII) to give compounds (IX), according to the conditions described above, as represented in Scheme 4:

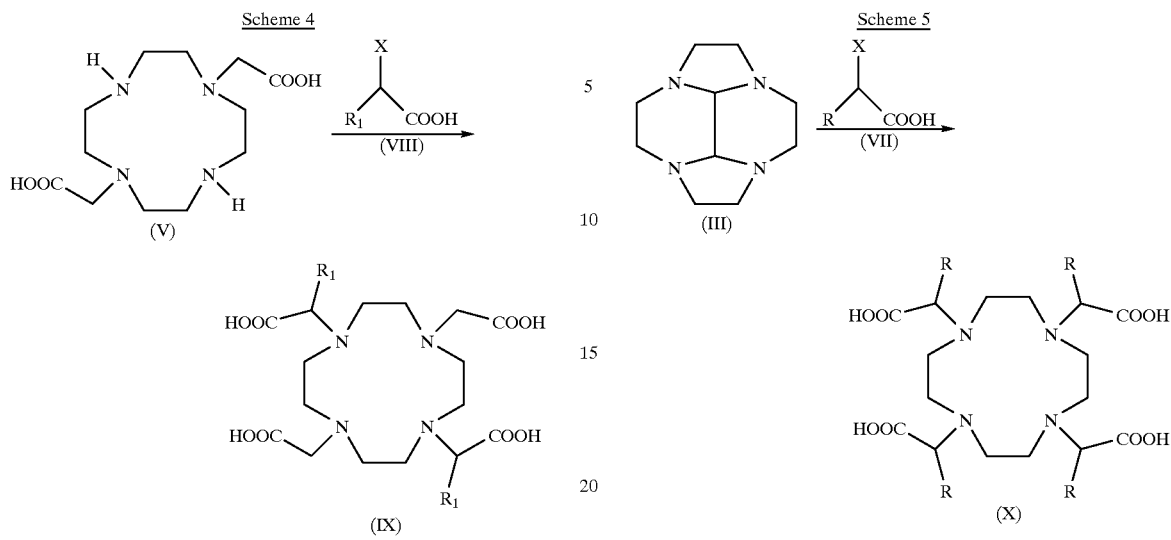

This process is particularly preferred when, in compound (VIII), $R_1$ corresponds to $R_2$. It is, in fact, more convenient to react the alkylating agent of formula (VIII) with the preformed 1,7-DO2A acid, than directly to react the tetracycle of formula (III) with the alkylating agent itself.

Particularly preferred is the process according to scheme 4 for the preparation of α1,α7-bis[(phenylmethoxy)methyl]-1,4,7,10-tetraazacyclododecane-1,4,7,10-tetraacetic acid, using as alkylating agent of formula (VIII) 2-bromo-3-(phenylmethoxy)propanoic acid methyl ester or 2-trifluoromethanesulfonate-3-(phenylmethoxy)propanoic acid methyl ester:

in which

R and X have the same meanings as defined above.

The amount of alkylating agent of formula (VII) ranges from 4 to 4.3 mols of reagent per mol of substrate.

The reaction temperature can vary from room temperature to 80° C., depending on the reactivity of the selected alkylating agent in the indicated conditions.

The basic pH in the reaction is preferably obtained by addition of an alkali or alkaline-earth metal hydroxide to the aqueous solution of compound (III).

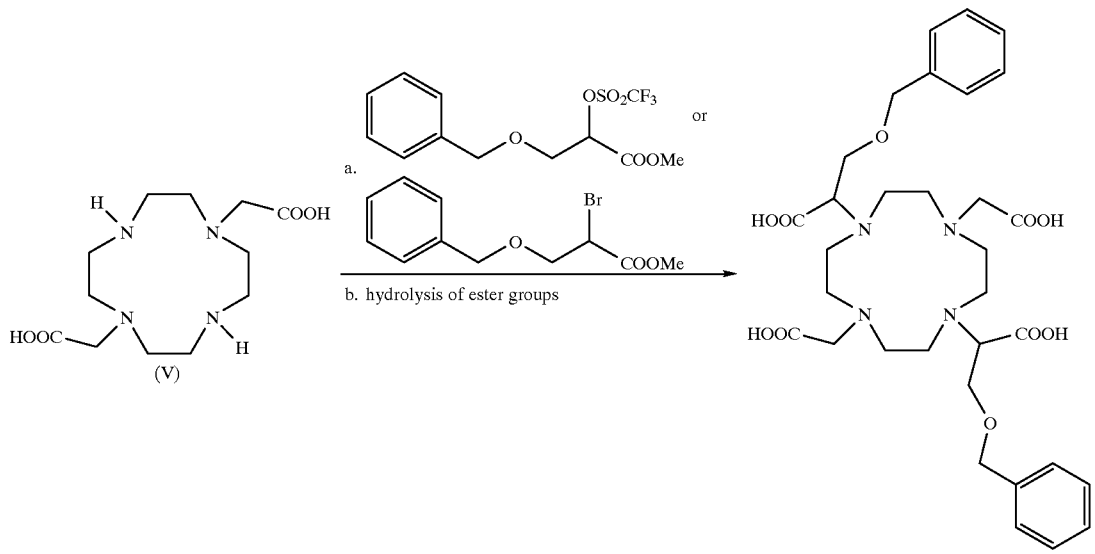

useful to obtain, after complexation with the suitable paramagnetic metal ion, preferably gadolinium, a contrast medium for magnetic resonance tomography, as described in EP 325762.

It is a further object of the present invention the process for the preparation of the compounds of general formula (X), by complete alkylation reaction with the acid of general formula (VII), as represented in Scheme 5.

Particularly preferred are sodium and potassium hydroxides.

Particularly preferred are the alkylating agents of formula (VII) in which the R group can be selected from the group consisting of: H or a straight alkyl group, such as a methyl, ethyl, propyl, isopropyl, butyl group, in its turn substituted by hydroxy groups or interrupted by oxygen atoms, as defined above.

The reactive group X can be selected, as above, from the group consisting of halogens (Cl, Br, I), or it is a mesylate, benzenesulfonyloxy, nitrobenzenesulfonyloxy, or tosylate group.

Particularly preferred are the compounds in which X is a halogen, more particularly a bromide, and the compounds of general formula (VII) deriving from bromoacetic or 2-bromopropionic acid.

Particularly preferred is the process for the preparation of compound (IV) by alkylation of compound (III) at basic pH with an acetic acid reactive derivative as represented in Scheme 6.

Scheme 6

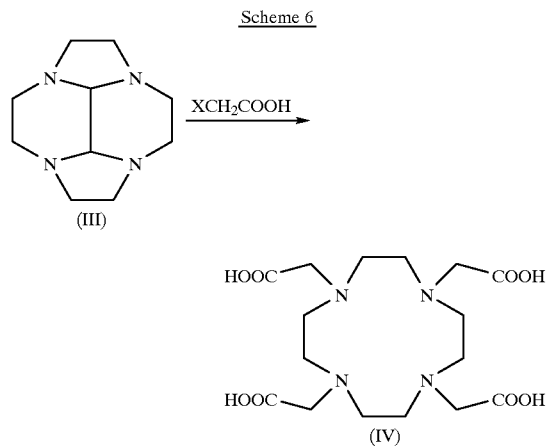

The conversion of compound (III) to compound (IV) requires heating (III) in aqueous solution at temperatures from 25 to 50° C., at basic pH (preferably pH 10–11), in the presence of an acetic acid reactive derivative, preferably a haloacetic acid, added in amounts of at least 4 mols per mol of compound (III).

At the end of the reaction, crude compound (IV) is precipitated by acidification, then it can be purified through ion exchange and water-recrystallization processes.

In the Experimental section, the synthesis of α,α',α",α"'-tetrametil-1,4,7,10-tetraazacyclododecane-1,4,7,10-tetraacetic acid according to scheme 5 is reported

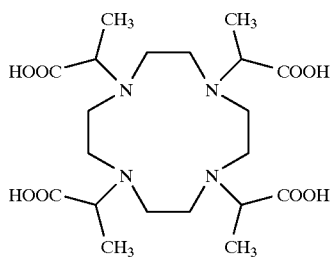

in which compound (III) is reacted with 2-bromopropionic acid.

In substance, intermediate (III) is a key intermediate to obtain 1,4,7,10-tetraazacyclododecane derivatives of formula (VI) both disubstituted at the 1- and 7-positions, and tetrasubstituted, without need for the macrocycle itself as an expensive starting product for the synthesis.

In the following, some examples of preparation according to the invention are reported.

The progress of the reactions is monitored by HPLC, using the following method:

Column: Polymer Labs PLRP-S 250×4 mm

Elution: isocratic

Mobile phase: A/B=99/1
  A: 50 mM $NH_4H_2PO_4$ adjusted to pH 4 with 85% $H_3PO_4$
  B: Methanol Temperature: 30° C.

Detection: 270 nm

Flow: 0.5 mL/min

Preparation of the sample: about 2 mg of product are placed in a 20 mL beaker, then 0.5 ml of an about 0.1M solution of $CuCl_2 \times 2H_2O$ are added, derivatizing for 15 min. at 35° C. The eluent is then added to the required volume.

EXPERIMENTAL SECTION

EXAMPLE 1

Preparation of 1,4,7,10-tetraazacyclododecane-1,7-diacetic acid

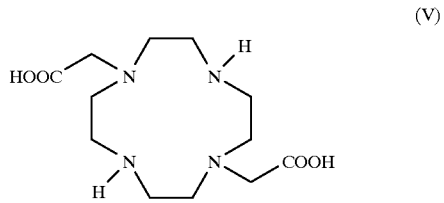

225 g (1.16 mol) of (III) (prepared as described in MI 96A 001257 and in MI 97A 000783) are dissolved in 200 g of water. Bromoacetic acid (80% sol.) (403 g; 2.32 mol) and 30% NaOH (to pH 10.3) are added at the same time, while keeping temperature at 20–25° C. The solution is heated to 50° C., and stirred at pH 10.3 for 5 h. When the reaction is completed, pH is adjusted to 6 with 34% HCl and the mixture is concentrated to dryness. The residue is dissolved in 250 ml of deionized water and percolated on IRA 420 resin (6 L) at a 0.03 BV/h flow, eluting with water and subsequently with 1N HCl. The fractions containing the product are concentrated and percolated on PVP resin (5 L) at a 0.07 BV/h flow. After elution with water, the fractions containing the product are combined and concentrated to dryness to obtain the desired product as a white solid (310 g; 1.075 mol).

Yield: 93%

The product can be crystallized from a Methanol:Acetone 8:2 v/v mixture.

Crystallization yield: 85%.

The $^1$H-NMR, $^{13}$C-NMR, IR and MS spectra are consistent with the indicated structure.

EXAMPLE 2

Preparation of α,α'-dimethyl-1,4,7,10-tetraazacyclododecane-1,7-diacetic acid

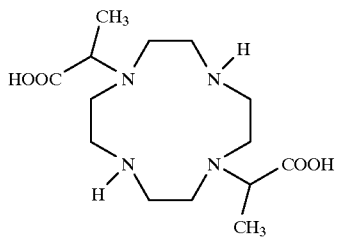

Analogously to the procedure described in Example 1, compound (III) is reacted with 2-bromopropionic acid to give the desired product.

Yield: 85%

The $^1$H-NMR, $^{13}$C-NMR, IR and MS spectra are consistent with the indicated structure.

EXAMPLE 3

Preparation of α,α'-diethyl-1,4,7,10-tetraazacyclododecane-1,7-diacetic acid

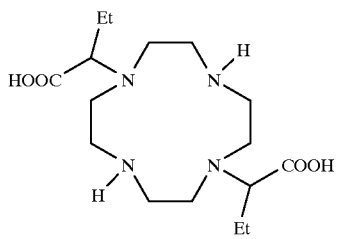

Analogously to the procedure described in Example 1, compound (III) is reacted with 2-bromobutyric acid to give the desired product.

Yield: 82%

The $^1$H-NMR, $^{13}$C-NMR, IR and MS spectra are consistent with the indicated structure.

EXAMPLE 4

Preparation of α1,α7-dimethyl-1,4,7,10-tetraazacyclododecane-1,4,7,10-tetraacetic acid

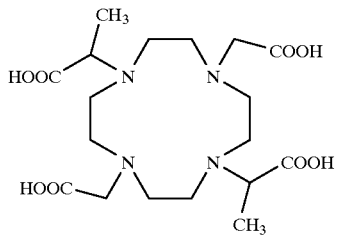

The basic aqueous solution of α,α'-dimethyl-1,4,7,10-tetraazacyclododecane-1,7-diacetic acid, prepared as described in Example 2, is reacted with bromoacetic acid, to obtain the desired product.

The $^1$H-NMR, $^{13}$C-NMR, IR and MS spectra are consistent with the indicated structure.

EXAMPLE 5

Preparation of α1,α7-diethyl-1,4,7,10-tetraazacyclododecane-1,4,7,10-tetraacetic acid

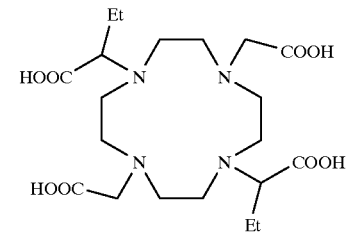

The basic aqueous solution of α,α'-diethyl-1,4,7,10-tetraazacyclododecane-1,7-diacetic acid, prepared as described in Example 3, is reacted with bromoacetic acid, to obtain the desired product.

The $^1$H-NMR, $^{13}$C-NMR, IR and MS spectra are consistent with the indicated structure.

EXAMPLE 6

Preparation of α1,α7-bis[[(phenylmethoxy)methyl]-1,4,7,10-tetraazacyclododecane-1,4,7,10-tetraacetic acid

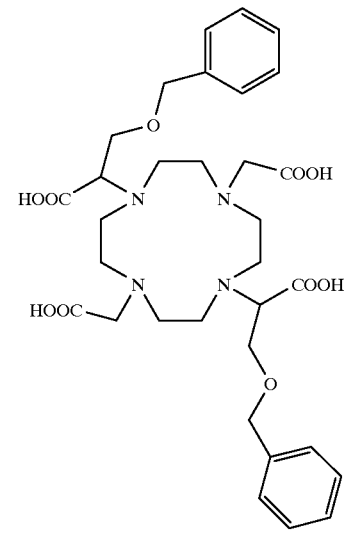

1,4,7,10-Tetraazacyclododecane-1,7-diacetic acid, prepared as described in Example 1, is reacted with 2-trifluoromethanesulfonate-3-(phenylmethoxy)propanoic acid methyl ester (prepared starting from the corresponding hydroxy derivative) in acetonitrile, in inert atmosphere at 10° C. and in the presence of diisopropylethylamine. At the end of the reaction, the mixture is concentrated to a residue which is dissolved in a NaOH aqueous solution and washed with chloroform to remove the excess of alkylating agent and diisopropylethylamine. The ester groups of the product contained in the alkaline aqueous phase are hydrolysed according to procedures known in literature. At the end of the hydrolysis, the product is precipitated by acidification to pH 3.5. The solid is filtered, washed with water on the filter and dried under vacuum, to obtain the desired product.

The $^1$H-NMR, $^{13}$C-NMR, IR and MS spectra are consistent with the indicated structure.

EXAMPLE 7

Preparation of 1,4,7,10-tetraazacyclododecane-1,4,7,10-tetraacetic acid

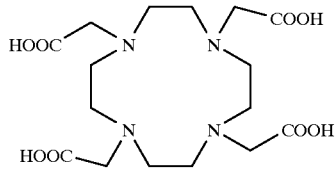
(I)

Into a reactor containing a solution of (III) (22.5 g; 0.116 mol) in 100 g of water, bromoacetic acid (sol. 80%) (80.6 g; 0.464 mol) and 30% NaOH (to pH 11) are dropped simultaneously at room temperature. The solution is heated to 45° C. and stirred at pH 11 for 5 h. When the reaction is completed, pH is adjusted to 2 with 34% HCl to precipitate a white solid, which is filtered through a porous filter, washed with a water/acetone 1.5/1 mixture and dried. The crude product is dissolved in water and percolated on PVP resin (0.5 L) at 0.5 BV/h flow. After elution with water, the fractions containing the product and free from inorganic salts are combined and concentrated to dryness to obtain the desired product as a white solid (44.4 g; 0.110 mol).

Yield: 95% (HPLC assay 98%)

The $^1$H-NMR, $^{13}$C-NMR, IR and MS spectra are consistent with the indicated structure.

EXAMPLE 8

Preparation of α,α',α'',α'''-tetramethyl-1,4,7,10-tetraazacyclododecane-1,4,7,10-tetraacetic acid

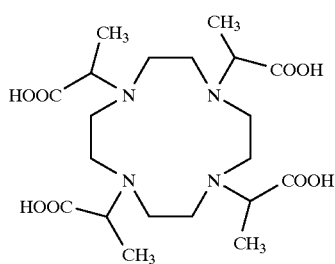

Analogously to the procedure described in Example 7, compound (III) is reacted with 2-bromopropionic acid, to obtain the desired product.

Yield: 80% (HPLC assay 97%)

The $^1$H-NMR, $^{13}$C-NMR, IR and MS spectra are consistent with the indicated structure.

We claim:

1. A process for the preparation of the compounds of general formula (I) and (II), comprising the steps represented in the following Scheme Scheme 1

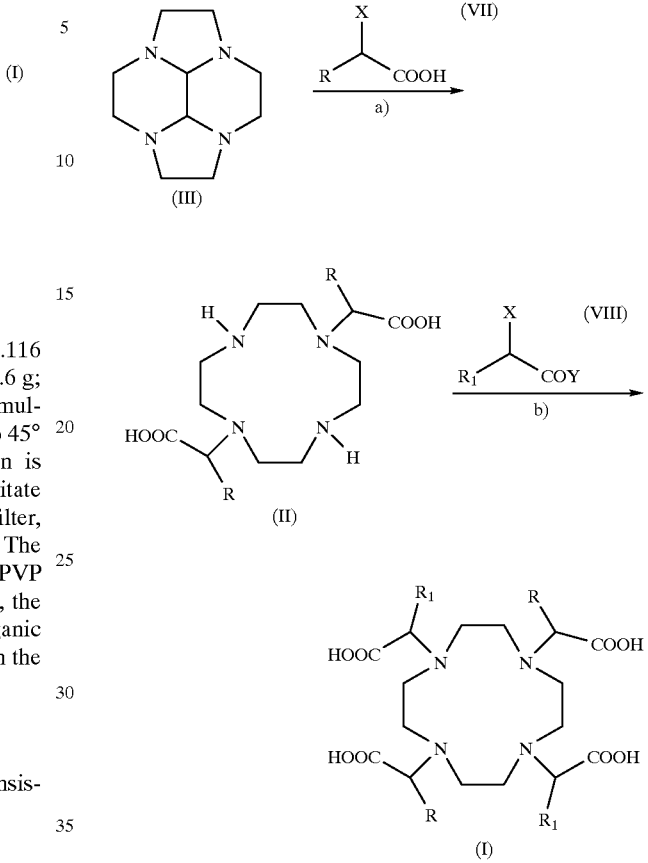

in which
R is a hydrogen atom, a straight, branched or cyclic $C_1$–$C_6$ alkyl group, unsubstituted or substituted with 1 to 10 oxygen atoms, $R_1$ independently of R, has the same meanings as R, or is a group $R_2$, in which $R_2$ is a $C_1$–$C_{20}$ alkyl group, optionally interrupted by a phenylene, a phenyloxy or phenylenedioxy, in its turn substituted with a straight or branched $C_1$–$C_6$ alkyl group, unsubstituted or substituted with 1 to 7 hydroxy groups or 1 to 3 $C_1$–$C_7$ groups; the aromatic group can be unsubstituted or substituted with alkoxy groups or halogens, carboxy, carbamoyl, alkoxycarbonyl, sulfamoyl, hydroxyalkyl, amino, acylamino, acyl, hydroxyacyl groups;

X is a halogen or a sulfonic acid reactive residue, and

Y is a —OH or —$OR_3$ group, wherein $R_3$ is a straight or branched $C_1$–$C_4$ alkyl group, in which:

step a) is the alkylation reaction of compound (III) with the acid of formula (VII), in aqueous solution and at basic pH, to give the compounds of formula (II), and step b) is the alkylation reaction of compounds of formula (II), according to known methods, with an $R_1$—CH(X)—COY alkylating agent of formula (VIII), followed by hydrolysis of any ester groups present, to give compounds (I).

2. A process as claimed in claim 1, in which the amount of alkylating agent of formula (VII) or (VIII) used ranges in step a) from 2 to 2.3 mols of reagent per mol of substrate and in step b) from 2 to 3 mols of reagent per mol of substrate.

3. A process as claimed in claim 1, in which the basic pH in step a) and in step b), when the alkylating agent of formula (VIII) is an acid, is obtained by addition of an alkali or alkaline-earth metal hydroxide to the aqueous solution of compounds (III) and (II).

4. A process as claimed in claim 3, in which the alkali or alkaline-earth metal hydroxides are selected from sodium and potassium hydroxides.

5. A process as claimed in claim 1, in which, when the alkylating agent of formula (VIII) is an ester derivative, the reaction solvent can be selected from dimethylformamide, dimethylacetamide, dimethylsulfoxide, acetonitrile and N-methylpyrrolidone, and the reaction is carried out in the presence of an aliphatic tertiary amine selected from triethylamine, diisopropylethylamine and tributylamine.

6. A process as claimed in claim 5, in which the alkylation reaction is followed by basic hydrolysis of the resulting diester, in conventional conditions, to obtain compound (I).

7. A process as claimed in claim 1, in which, in the alkylating agents of formula (VII) or (VIII), R is selected from the group consisting of: H or a straight or branched alkyl group, such as a methyl, ethyl, propyl, isopropyl, butyl, isobutyl group, in its turn substituted with hydroxy groups or interrupted by oxygen atoms; $R_2$ is selected from the group consisting of: phenyl, benzyl, phenylmethoxymethyl; $R_3$ is selected from the group consisting of: methyl, ethyl, isopropyl, butyl, tert-butyl; the reactive group X is selected from the group consisting of halogens (Cl, Br, I), or is a mesylate, benzenesulfonyloxy, nitrobenzenesulfonyloxy, tosylate or triflate group.

8. A process as claimed in claim 7, in which X is a bromide or a triflate group.

9. A process as claimed in claim 7, in which the alkylating agents of formula (VII) and (VIII) are selected from the group consisting of: bromoacetic acid, 2-bromopropionic acid, 2-bromobutyric acid.

10. A process as claimed in claim 7, in which the alkylating agent of formula (VIII) is selected from 2-bromo-3-(phenylmethoxy)propanoic acid methyl ester and 2-trifluoromethanesulfonate-3-(phenylmethoxy)propanoic acid methyl ester.

11. A process as claimed in claim 1, for the preparation of 1,4,7,10-tetraazacyclododecane-1,4,7,10-tetraacetic acid derivatives of formula (IX) starting from compounds (II), as represented in the following Scheme:

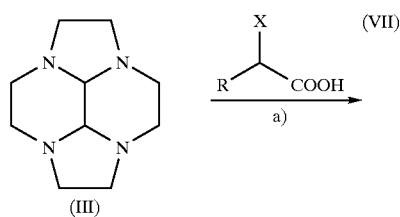

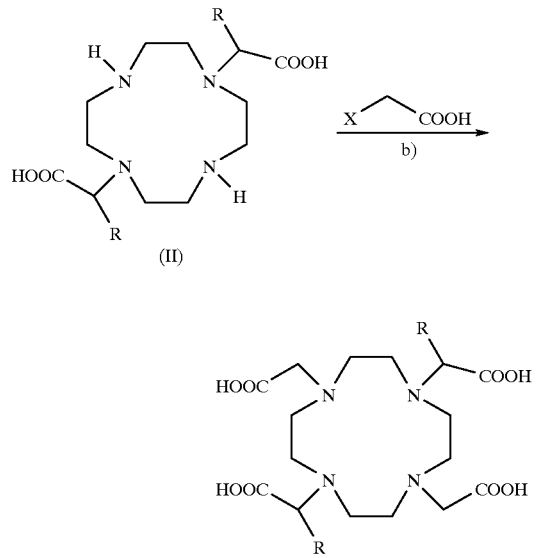

in which R and X have the meanings defined in claim 1, and step b) is the alkylation reaction of compounds (II), in aqueous solution at basic pH, with an alkylating agent X—CH$_2$COOH, to give compounds (IX).

12. A process as claimed in claim 11, for the preparation of the following compounds:
α,α'-dimethyl-1,4,7,10-tetraazacyclododecane-1,7-diacetic acid;
α,α'-diethyl-1,4,7,10-tetraazacyclododecane-1,7-diacetic acid;
α1,α7-dimethyl-1,4,7,10-tetraazacyclododecane-1,4,7,10-tetraacetic acid;
α1,α7-diethyl-1,4,7,10-tetraazacyclododecane-1,4,7,10-tetraacetic acid.

13. A process as claimed in claim 1, for the preparation of 1,4,7,10-tetraazacyclododecane-1,7-diacetic acid of formula (V) by alkylation of compound (III) with an acetic acid reactive derivative, as represented in the following Scheme:

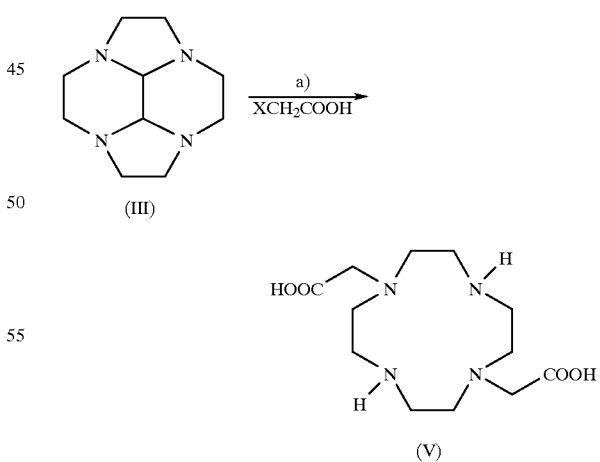

in which X and step a) have the meanings defined in claim 1.

14. A process as claimed in claim 13, in which the conversion of compound (III) to compound (V) is carried out by heating compound (III) in aqueous solution at temperatures from 25° C. to 50° C., at pH from 10 to 11, in the presence of a haloacetic acid added in amounts of 2 mol/mol of compound (III).

15. A process as claimed in claim 1, in which compound (V), obtained according to the process of claims 13–14, is alkylated with compound (VIII) to give compounds (IX), as represented in the following Scheme:

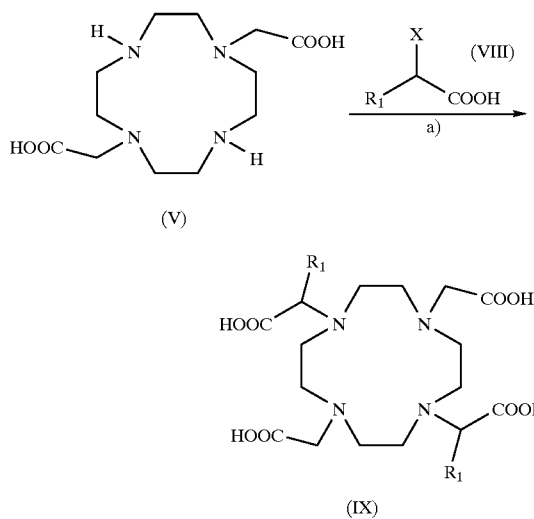

(IX)

in which X, $R_1$ and step a) have the meanings defined in claim 1.

16. A process as claimed in claim 15, in which $R_1$ is the same as $R_2$.

17. A process as claimed in claim 15, for the preparation of α1,α7-bis[(phenylmethoxy)methyl]-1,4,7,10-tetraazacyclododecane-1,4,7,10-tetraacetic acid, using 2-bromo-3-(phenylmethoxy)propanoic acid methyl ester or 2-trifluoromethanesulfonate-3-(phenylmethoxy)propanoic acid methyl ester as alkylating agent of formula (VIII):

and in which the alkylation reaction is followed by basic hydrolysis of the obtained diester intermediate in conventional conditions.

18. A process as claimed in claim 1 for the preparation of compounds (X) by complete alkylation of compound (III) with the alkylating agent of formula (VII), in aqueous solution and at basic pH, as represented in the following Scheme:

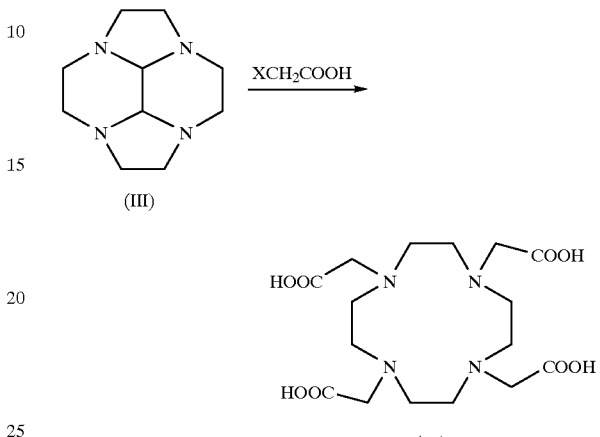

in which R and X have the same meanings as defined in claim 1.

19. A process as claimed in claim 18, in which the amount of alkylating agent of formula (VII) ranges from 4 to 4.3 mols of reagent per mol of substrate.

20. A process as claimed in claim 18, in which the basic pH in the reaction is obtained as claimed in claims 3 and 4.

21. A process as claimed in claim 18, in which, in the alkylating agent of formula (VII), R group is selected from the group consisting of: H or a straight alkyl group, such as a methyl, ethyl, propyl, isopropyl, butyl group, in its turn substituted with hydroxy groups or interrupted by oxygen atoms; X is selected from the group consisting of halogens (Cl, Br, I), or is a mesylate, benzenesulfonyloxy, nitrobenzenesulfonyloxy, tosylate group.

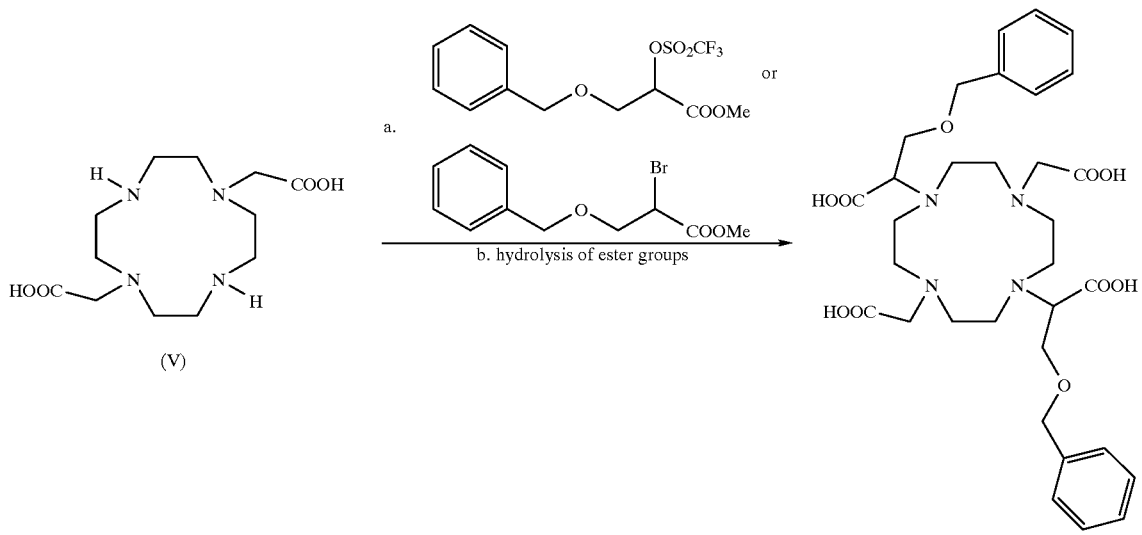

22. A process as claimed in claim 18, in which the alkylating agent of formula (VII) is a bromoacetic or 2-bromopropionic acid derivative.

23. A process as claimed in claim 18 for the preparation of 1,4,7,10-tetraazacyclododecane-1,4,7,10-tetraacetic acid of formula (IV) by alkylation of compound (III) at basic pH with an acetic acid reactive derivative, as represented in the following Scheme:

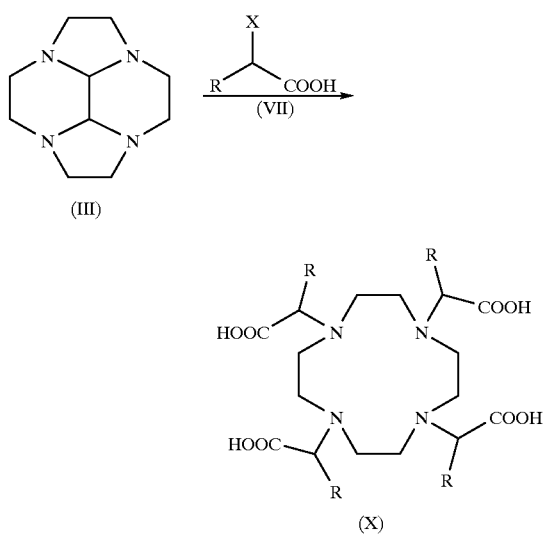

24. A process as claimed in claim 18 for the preparation of 1,4,7,10-tetraazacyclododecane-1,4,7,10-tetraacetic acid of formula (IV) by alkylation of compound (III) at basic pH with an acetic acid reactive derivative as represented in the following Scheme:

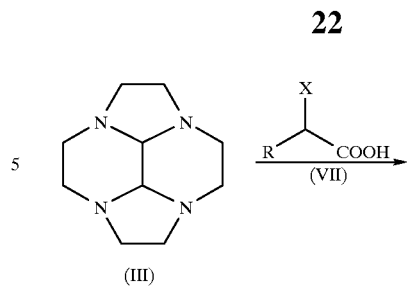

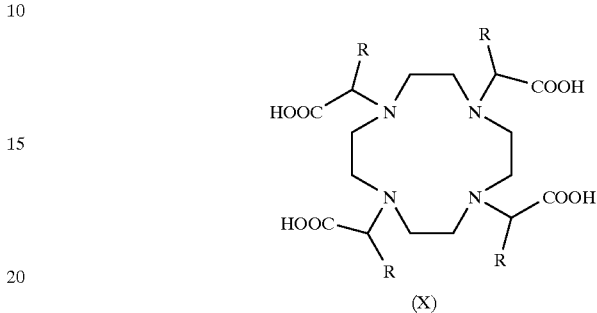

wherein the conversion of compound (III) to compound (V) is carried out by heating compound (III) in aqueous solution at temperatures from 25 to 50° C., at pH from 10 to 11, in the presence of 4 to 4.3 mols of a haloacetic acid per mol of substrate.

25. A process as claimed in claim 22, for the preparation of α,α',α'',α''-tetramethyl-1,4,7,10-tetraazacyclododecane-1,4,7,10-tetraacetic acid, in which compound (III) is reacted with 2-bromopropionic acid.

* * * * *